US009478209B2

(12) United States Patent
Wurm

(10) Patent No.: US 9,478,209 B2
(45) Date of Patent: Oct. 25, 2016

(54) TUNABLE ACTIVE NOISE CONTROL

(71) Applicant: Harman Becker Automotive Systems GmbH, Karlsbad (DE)

(72) Inventor: Michael Wurm, Straubing (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 657 days.

(21) Appl. No.: 13/683,708

(22) Filed: Nov. 21, 2012

(65) Prior Publication Data

US 2013/0129108 A1 May 23, 2013

(30) Foreign Application Priority Data

Nov. 22, 2011 (EP) .................................... 11190092

(51) Int. Cl.

| | |
|---|---|
| ***A61F 11/06*** | (2006.01) |
| ***G10K 11/16*** | (2006.01) |
| ***G10K 11/178*** | (2006.01) |
| *H04R 3/00* | (2006.01) |
| *H04R 1/10* | (2006.01) |

(52) U.S. Cl.

CPC ............. *G10K 11/16* (2013.01); *G10K 11/178* (2013.01); *G10K 11/1786* (2013.01); *G10K 2210/128* (2013.01); *G10K 2210/1282* (2013.01); *G10K 2210/3014* (2013.01); *G10K 2210/3017* (2013.01); *G10K 2210/3028* (2013.01); *H04R 1/1083* (2013.01); *H04R 3/005* (2013.01)

(58) Field of Classification Search

CPC ............... G10K 11/16; G10K 11/178; G10K 11/1786; G10K 2210/3014; G10K 2210/1282; G10K 2210/3017; G10K 2210/3028; G10K 2210/128; G10K 2210/30232; G10K 11/1784; G10K 11/1788; H04R 1/1083; H04R 3/005

USPC ............................ 381/71.1–71.4, 71.7–71.9, 381/71.11–71.14, 86, 94.1, 99, 98, 122, 150

See application file for complete search history.

(56) References Cited

U.S. PATENT DOCUMENTS

| | | | | |
|---|---|---|---|---|
| 5,848,169 | A | 12/1998 | Clark et al. | |
| 6,275,592 | B1 | 8/2001 | Vartiainen | |
| 7,062,049 | B1 * | 6/2006 | Inoue et al. | 381/71.4 |
| 2001/0005814 | A1 | 6/2001 | Dussac | |
| 2005/0207585 | A1 * | 9/2005 | Christoph | 381/71.11 |
| 2008/0181422 | A1 * | 7/2008 | Christoph | 381/73.1 |
| 2010/0124337 | A1 | 5/2010 | Wertz et al. | |
| 2011/0235693 | A1 * | 9/2011 | Lee et al. | 375/224 |

FOREIGN PATENT DOCUMENTS

| | | |
|---|---|---|
| JP | H07104770 A | 4/1995 |
| JP | H11149292 A | 6/1999 |

OTHER PUBLICATIONS

Kuo et al., "Active Noise Control: A Tutorial Review", Proceedings of the IEEE, vol. 87, No. 6, Jun. 1999.

Extended European Search Report for corresponding Application No. 111900924, mailed Aug. 29, 2012, 8 pages.

Japanese Office Action for corresponding Application No. 2012-255297, mailed Dec. 24, 2013, 7 pages.

* cited by examiner

*Primary Examiner* — Vivian Chin
*Assistant Examiner* — Con P Tran
(74) *Attorney, Agent, or Firm* — Brooks Kushman P.C.

(57) ABSTRACT

An active noise control system and method for tuning an acoustic noise signal at a listening position are disclosed in which a first weighting element is connected in the filter coefficient copy path and/or a second weighting element is connected in the microphone path.

15 Claims, 4 Drawing Sheets

TUNABLE ACTIVE NOISE CONTROL

CLAIM OF PRIORITY

This patent application claims priority from EP Application No. 11 190 092.4 filed Nov. 22, 2011, which is hereby incorporated by reference.

FIELD OF TECHNOLOGY

The present invention relates to the field of active audio noise control, and in particular to tunable multiple-channel noise control systems and methods.

RELATED ART

Acoustic noise problems are becoming more and more evident as an increasing amount of industrial equipment such as engines, blowers, fans, transformers, and compressors are being used. The traditional approach to acoustic noise control uses passive techniques such as enclosures, barriers, and silencers to attenuate the undesired noise. These passive silencers are valued for their high attenuation over a broad frequency range; however, they are relatively large, costly, and ineffective at low frequencies. Mechanical vibration is another related type of noise that commonly creates problems in all areas of transportation and manufacturing, as well as in many household appliances. Active noise control (ANC) involves an electroacoustic or electromechanical system that cancels the primary (unwanted) noise based on the principle of superposition; specifically, an antinoise of equal amplitude and opposite phase is generated and combined with the primary noise, thus resulting in the cancellation of both noises. The ANC system efficiently attenuates low-frequency noise where passive methods are either ineffective or tend to be relatively expensive or bulky. ANC permits improvements in noise control, often with potential benefits in size, weight, volume, and cost.

A basic design of acoustic ANC utilizes a microphone, a filter and a secondary source such as a loudspeaker to generate a canceling sound. Since the characteristics of the acoustic noise source and the environment are time varying, the frequency content, amplitude, phase, and sound velocity of the undesired noise are nonstationary. An ANC system must therefore be adaptive in order to cope with these variations.

Multi-channel active noise control is achieved by introducing a canceling "antinoise" wave through an appropriate array of secondary sources. These secondary sources are interconnected through an electronic system using digital signal processing for the particular cancellation scheme. The basic adaptive algorithm for ANC has been developed and analyzed based on single-channel broad-band feedback or feedforward control as set forth by, e.g., S. M. Kuo, D. R. Morgan, "*Active Noise Control: A Tutorial Review*", PROCEEDINGS OF THE IEEE, VOL. 87, NO. 6, June 1999. These single-channel ANC solutions are expanded to multiple-channel cases using various online secondary-path modeling techniques and special adaptive algorithms, such as lattice, frequency-domain, subband, and recursive-least-squares. In numerous situations, however, it is not desired to cancel all noise but to modify the noise in order to be perceived as more pleasant by a listener.

There is a need for tunable noise control systems and methods that are suitable also for multi-channel applications.

SUMMARY OF THE INVENTION

An active noise control system for tuning an acoustic noise signal at a listening position comprises a microphone that converts acoustic signals into electric signals and that is arranged at the listening position; a loud-speaker that converts electrical signals into acoustic signals and that radiates a noise cancelling signal via a second path to the microphone; a secondary noise source that generates an electrical noise signal modeling the acoustic noise signal; a first filter that has a controllable first transfer characteristic and that is connected between the secondary noise source and the loudspeaker; a second filter that has a second transfer characteristic and that is connected downstream of the secondary noise source; a third filter that has a controllable third transfer characteristic and that is connected downstream of the second filter; a noise signal estimator that is connected downstream of the microphone and that provides an estimate of the acoustic noise signal; and an adaptive filter controller that is downstream of the second filter and downstream of the noise signal estimator and that controls the transfer characteristic of the third filter. The second transfer characteristic is an estimation of the transfer characteristic of the secondary path. The first transfer characteristic is controlled by the third transfer characteristic via a filter coefficient copy path. A first weighting element is connected into the filter coefficient copy path and/or a second weighting element is connected downstream of the noise signal estimator.

In a second embodiment, an active noise control method for tuning an acoustic noise signal at a listening position comprises converting acoustic signals at the listening position into electric signals; generating an electrical noise signal modeling the acoustic noise signal; filtering the electrical noise signal that models the acoustic noise signal with a controllable first transfer characteristic to provide a first filtered noise signal; converting the first filtered noise signal into an acoustic signal which is radiated via a second path to the listening position; filtering the electrical noise signal that models the acoustic noise signal with a second transfer characteristic to provide a second filtered noise signal; adaptively filtering with a third transfer characteristic the second filtered noise signal; providing an estimate of the acoustic noise signal from the converted acoustic signal at the listening position. The second transfer characteristic is an estimate of the transfer characteristic of the secondary path. The first transfer characteristic is controlled by the third transfer characteristic via a filter coefficient copy path. A first weighting process is performed in the filter coefficient copy path and/or a second weighting process is applied to the estimate of the acoustic noise signal.

These and other objects, features and advantages of the present invention will become apparent in light of the detailed description of the embodiments thereof, as illustrated in the accompanying drawings. In the figures, like reference numerals designate corresponding parts.

DESCRIPTION OF THE DRAWINGS

Various specific embodiments are described in more detail below based on the exemplary embodiments shown in the figures of the drawing. Unless stated otherwise, similar or identical components are labeled in all of the figures with the same reference numbers.

DETAILED DESCRIPTION OF THE INVENTION

In the following description, noise is defined as any kind of undesirable disturbance, whether it is created by electrical or acoustic sources, vibration sources, or any other kind of media. Therefore, ANC algorithms disclosed herein can be applied to different types of noise using appropriate sensors and secondary sources.

Figure 1:
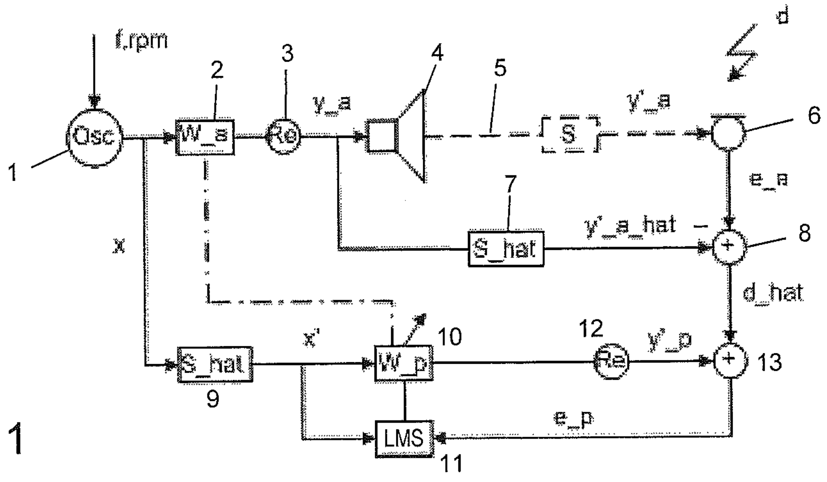
FIG. 1 is a block diagram illustration of a basic single-channel feedforward ANC system.

FIG. 1 illustrates the signal flow in a basic single-channel feedforward ANC system for generating a compensation signal that at least partially compensates for, eliminates or modifies an undesired acoustic disturbance signal d. An electrical noise signal, i.e., a complex reference noise signal x, representative of the disturbing noise signal d is generated by a secondary noise source 1 such as a synthesizer or signal generator and may model, for example, acoustic signals generated by mechanical vibrations of an engine, sound of components mechanically coupled thereto such as a fan, etc. To approximate the disturbing noise signal d from one or more of such sources of acoustic noise by the reference noise signal x, the noise generator 1 may be coupled to a dedicated sensor (not shown) such as microphone, an rpm meter or any other sensor that provides a signal corresponding to the acoustic noise signal. For instance, an oscillator may be used as the secondary noise source 1 which is intended to represent a vehicle engine and which is controlled by a signal representing the revolutions per minute rpm of the engine and/or its fundamental frequency f.

In the ANC system of FIG. 1, the electrical noise signal x from the secondary noise source 1 is processed by a filter 2 and a subsequent real part processor 3 to provide a compensation signal y_a to a loudspeaker 4 that radiates the compensation signal y_a along a secondary path 5 to a listening position where a microphone 6 is positioned. The microphone 6 senses at the listening position, the disturbance noise signal d and delayed compensation signal y'_a interfere with each other resulting in an error signal e_a that is provided by the microphone; the interaction of both signals can be described mathematically as signal addition. The (acoustic) error signal e_a is transferred by the microphone 6 into an electrical error signal which, for the sake of simplicity, is herein also referred to as error signal e_a.

The compensation signal y_a is also supplied to a filter 7 to generate a compensation signal y_a_hat therefrom, which is subtracted from the error signal e_a by a subtractor 8 to provide an electrical disturbance signal d_hat. The filter 7 and the subtractor 8 form an estimator that provides an estimate of the acoustic disturbance signal d, i.e., electrical disturbance signal d_hat. However, any other type of estimator may be used.

The reference noise signal x is supplied to a filter 9 that provides a modified noise signal x', which is provided to an adaptive filter having a controlled filter 10 and a filter controller 11. Adaptive filters adjust (e.g., with their filter controller 11) their coefficients (in their controlled filter 11) to minimize an error signal, and adaptive filters can be realized for example as (transversal) finite impulse response (FIR), (recursive) infinite impulse response (IIR), lattice, or transform-domain filters. The most common form of adaptive filter is the transversal filter using the least-mean-square (LMS) algorithm. In the present example, the modified noise signal x' is supplied to both the controlled filter 10 and the filter controller 11, whereby the filter controller 11 controls the controlled filter 10, i.e., adapts the filter coefficients of the controlled filter 10. The controlled filter 10 together with a subsequent real part processor 12 provides a signal y'_p to an adder 13, which also receives the electrical disturbance signal d_hat. In addition to the signal x', the filter controller 11 also receives a modified error signal e_p from the adder 13 (at its error signal input).

The controlled filter 10 has a transfer characteristic W_p and the filter 2 has a transfer characteristic W_a, which is a copy of the transfer characteristic W_p of the controlled filter 10, i.e., both characteristics are identical or the transfer characteristic W_a is updated on a regular basis by the transfer characteristic W_a. Matching of the filters is performed via a filter coefficient copy path between the filters 2 and 10. The filters 7 and 9 both have an identical transfer characteristic S_hat that is an approximation of a transfer characteristic S of the secondary path 5. Accordingly, the ANC system of FIG. 1 has a so-called double structure with active and passive filter branches. The active filter branch is established by the controlled filter 2 in connection with the filter controller 11, and the passive branch is established by the filter 10. The adaptive filter, i.e., controlled filter 10 in connection with filter controller 11, adapts the filter coefficients and copies or transfers via a coefficient copy path these coefficients into filter 2.

The adaptive filter 10 in connection with the real part processor 12 generates from the complex reference noise signal x' the real signal y'_p, which ideally is identical with or at least rather similar to disturbing noise signal d. In an ideal adapted system the following relations apply:

$$y'\_p=-d\_\text{hat}$$

$$Re\{x'\cdot W\_p\}=-d\_\text{hat}$$

$$Re\{x\cdot S\_\text{hat}\cdot W\_p\}=-d\_\text{hat}$$

in which the active branch may be identical with the passive branch:

$$W\_a=W\_p.$$

Adaption is performed in the present case according to a least-mean-square (LMS) algorithm in a time-discrete manner, according to which:

$$W\_p[n]=W\_p[n-1]+\mu\cdot x'\cdot e\_p,$$

in which μ stands for the step size of the LMS algorithm that controls the amount of gradient information used to update each coefficient.

The single-channel ANC system described above with reference to FIG. 1 generates the complex reference noise signal x with a secondary noise generator, e.g., a sinus-cosinus oscillator, whose frequency corresponds to the rpm of a vehicle engine. The system shown is a narrowband ANC system for the reduction or cancellation of narrowband sinusoid noise signals such as harmonic sound components of a rotating engine. In vehicles with motors such systems are used to cancel certain harmonics of a fundamental oscillation. For the fundamental, and some or each of the harmonics, such single-channel ANC system may be employed, constituting a simple multi-channel ANC system. The noise signal fundamental and its harmonics can be described as follows:

$$f_m = m \cdot \text{rpm}/60 \text{ with } m=1, 2, 3 \ldots,$$

in which $f_m$ is the frequency of the m-th harmonic with the first harmonic (m=1) being the fundamental and rpm are the revolutions per minute.

In the present example, an orthogonal signal generated by the oscillator in connection with complex filters are used so that the adaptive filter and its shadow filter each have a double set of filter coefficients, one for the real part and one for the imaginary part of the complex oscillator signal, i.e., reference noise signal x. However, the complex filter may produce a complex output signal even when its input signal is real. The reference noise signal x can be described as follows:

$$x = e^{jwn} = \cos(w \cdot n) + j \sin(w \cdot n) \text{ with}$$

$$w = 2\pi f_m / f_s,$$

in which $f_m$ is the frequency of the orthogonal noise signal, n is the discrete time index and $f_s$ stands for the sample rate of the system.

Accordingly, the complex adaptive transfer characteristics W_a and W_p are:

$$W\_a = w\_a\_re + j \cdot w\_a\_im,$$

$$W\_p = w\_p\_re + j \cdot w\_p\_im.$$

Finally, an operator Re of the real part processors 3 and 12 can be described by $$Re(A \cdot e^{jx}) = A \cos(x).$$

The real part processors 3 and 12 convert complex signals into real signals that are to be radiated by the loudspeaker 4. Processing of complex signals with subsequent conversion into real signals is an efficient way of implementing such a signal processing system.

The secondary path 5 has a transfer characteristic S and represents the path between the input circuit of the loudspeaker 4 (including digital-analog converters, amplifiers etc.) and the output circuit of the microphone 6 (including amplifiers, analog-digital converters, etc.), or in terms of signals, between the, e.g., digital signals y_a and e_a. The filters 7 and 9 each have a transfer characteristic S_hat and model the secondary path 5. Accordingly, electrical signal d_hat models/estimates the acoustic disturbance signal d. If S_hat=S, then d_hat=d. d_hat is the target for adaption of the adaptive filter (10, 11), also referred to as the desired signal for adaption of the transfer characteristic W_a and, thus, W_p. Reference signal x' for the adaptive filter is derived from the reference noise signal x by filtering signal x with the transfer characteristic S_hat. The filtering may be performed in the time or spectral domain using discrete convolution (conv) or complex multiplication. If filtering is performed in the spectral domain, a coefficient corresponding to the transfer characteristic S_hat at frequency $f_m$ of signal x is to be used instead and, accordingly, is to be input. The reference noise signal x is input into the (adaptive) filter 2 which compensates for deviations from the actual secondary path 5 having transfer characteristic S, i.e., reference noise signal x is adapted to be the negative of signal d. Signal y'_a is the "real" analog cancelling signal (also referred to as ANC output signal) at the position of the microphone 6.

Figure 2:
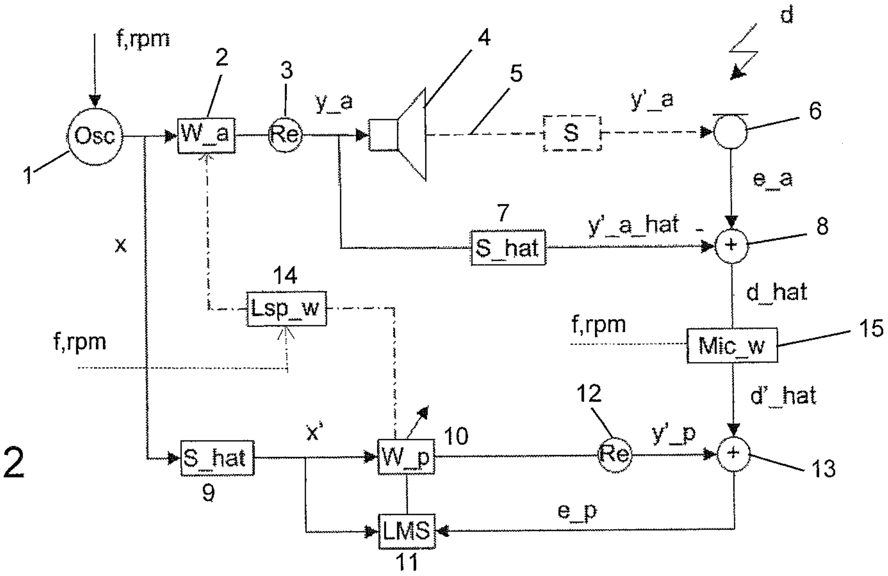
FIG. 2 is a block diagram illustration of a modified ANC system as shown in FIG. 1.

Referring now to FIG. 2, the system of FIG. 1 may be enhanced with additional weighting elements 14 and 15 which are, for instance, coefficient elements that multiply the corresponding input signals with a constant Lsp_w or Mic_w, respectively. The weighting element 14 having the weighting coefficient Lsp_w is connected between the filters 10 and 2 to transfer the filter coefficients of the filter 10 to the filter 2, thereby changing the filter coefficients. The weighting element 15 having the weighting coefficient Mic_w is connected between the subtractor 8 and the adder 13 to change signal d_hat provided by the subtractor 8 into signal d'_hat that is fed into the adder 13.

The system of FIG. 2 allows for adjusting the characteristic of an ANC system to personal preferences by changing the weighting coefficients Lsp_w and Mic_w. The estimated disturbance signal d_hat is multiplied with the weighting coefficient Mic_w so that the passive filter branch, in particular the filter 10 in connection with filter the controller 11, adapts to this weighted disturbance signal d'_hat and provides a signal y'_p which is:

$$y'\_p = -Mic\_w \cdot d\_\text{hat}.$$

Alternatively or additionally to weighting of the passive branch, the active branch, in particular the adaptive filter 2, may be weighted by, e.g., multiplying the copied filter coefficients of the filter 10 with the weighting coefficient(s) Lsp_w, so that $$y'\_a \sim Lsp\_w \cdot y'\_p.$$

Provided the transfer characteristic S_hat is an exact model (estimation) of the secondary path transfer characteristic S and the system is in a steady state and has reached a certain degree of adaptation, the weighting coefficients Lsp_w and Mic_w may be selected according to the following considerations:

1. Attenuation is adjusted through Mic_w a. Attenuation at the position where the microphone 6 is located can be adjusted by the weighting coefficient Mic_w being between 0 and 1 including 0 (=no attenuation) and 1 (=maximum attenuation). In turn, the resulting amplification V (of disturbance signal d) is accordingly:

$$V\,[\text{dB}] = 20 \cdot \log 10(a) = 20 \cdot \log 10(1 - Mic\_w)$$

$$0 \le Mic\_w < 1.$$

b. Amplification at the position where the microphone 6 is located can be adjusted by the weighting coefficient Mic_w being between 0 and −∞ including 0 (=minimum amplification) and −∞ (=maximum amplification). The resulting amplification level V (based on the amplification a) is accordingly:

$$V\,[\text{dB}] = 20 \cdot \log 10(a) = 20 \cdot \log 10(1 - Mic\_w)$$

$$0 > Mic\_w > -\infty.$$

For the above considerations (1a and 1b), the following conditions ideally are assumed:

$$Lsp\_w = 1$$

$$a = e\_a/d = (d + y'\_a)/d \approx (d + y'\_p)/d$$

$$d\_\text{hat} \approx d$$

$$d'\_\text{hat} = Mic\_w \cdot d\_\text{hat}$$

y'_d≈−d'_hat $a \approx (d - Mic\_w \cdot d)/d = 1 - Mic\_w.$

2. Attenuation is adjusted through Lsp_w a. Attenuation at the position where the microphone 6 is located can be adjusted by the weighting coefficient Lsp_w being between 0 and 1 including 0 (=no attenuation) and 1 (=maximum attenuation). In turn, the resulting amplification level V (based on the amplification a) is accordingly:

$V\,[\mathrm{dB}] = 20 \cdot \log 10(a) = 20 \cdot \log 10(1 - Lsp\_w)$

0≤Lsp_w<1.

b. Amplification at the position where the microphone 6 is located can be adjusted by the weighting coefficient Lsp_w being between 0 and −∞ including 0 (=minimum amplification) and −∞ (=maximum amplification). The resulting amplification V is accordingly:

$V\,[\mathrm{dB}] == 20 \cdot \log 10(a) = 20 \cdot \log 10(1 - Lsp\_w)$

0>Lsp_w>−∞.

For the above considerations (2a and 2b), the following conditions ideally are assumed:

Mic_w=1

$a = e\_a/d = (d + y'\_a)/d \approx (d + Lsp\_w \cdot y'\_p)/d$ d_hat≈d $d'\_\mathrm{hat} = Mic\_w \cdot d\_\mathrm{hat}$ $y'_{13}$ p≈−d'_hat $a \approx (d - Lsp\_w \cdot d)/d = 1 - Lsp\_w.$ A major advantage of the system described above with reference to FIG. 2 is that microphone and loudspeaker can be adjusted independently from each other and that the user can decide what to put emphasis on, the loudspeaker 4 or the microphone 6. Particularly in multichannel ANC systems it is advantageous when, for instance, a certain loudspeaker (e.g., corresponding to a rear or front position within a vehicle cabin) or a certain microphone (e.g., corresponding to the driver's position) can be independently (and absolutely) selected regarding their contribution to and utilization for the noise reduction or enhancement at the available microphone positions of the ANC system. The system allows the listener, e.g., the vehicle passengers to freely set the desired noise reduction or noise enhancement or, in other words, the perceived noise signal. As weighting is performed by multiplications, it can be implemented in digital signal processors relatively simply. Suitable weighting coefficients Mic_w and Lsp_w for different situations (e.g., fundamental frequency $f_0$ or order frequency $f_m$, revolutions per minute rpm, etc.) may be stored in a memory in the form of a table and may be read out depending on the situation (e.g., fundamental frequency $f_0$ or order frequency $f_m$, revolutions per minute rpm, etc.) that has been detected.

Figure 3:
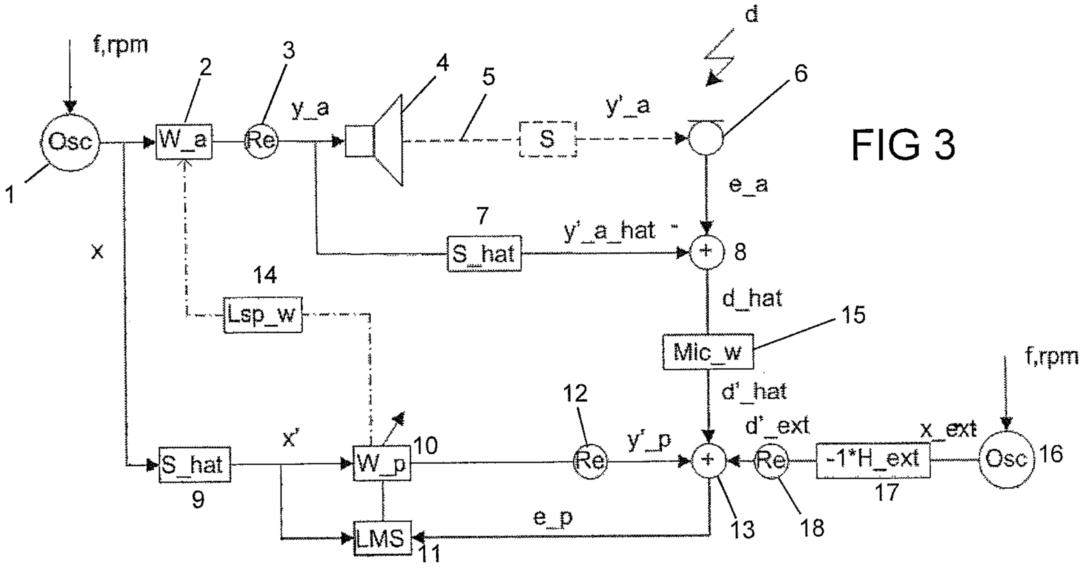
FIG. 3 is a block diagram illustration of a modified ANC system as shown in FIG. 2.

Referring now to FIG. 3, the system of FIG. 2 may be enhanced by an external secondary noise source 16 that generates an external reference noise signal x_ext and an external filter 17 connected downstream of the noise source 16 and having a transfer characteristic −1.H_ext. A real part processor 18 is connected between the external filter 17 and the adder 13, supplying the adder with a signal d'_ext. The adder adds this signal d'_ext to the signals y'_p and d'_hat so that the passive branch now provides a signal y'_p which is $y'\_p = -(d'\_\mathrm{hat} + d'\_\mathrm{ext}).$ Assuming that Lsp_w=1, the signal y'_p as defined above will be part of the signals y'_a and e_a. Thus, any (e.g., harmonic) signal desired by the listener can be added to the noise. The filter 17 is used to alter the signal d'_ext respective of amplitude and phase, if desired. As can be seen, the additional, external signal d'_ext does not have any effect on disturbance signal d per se. Altering of the disturbance signal d is only performed by the ANC system independent of its system structure.

Figure 4:
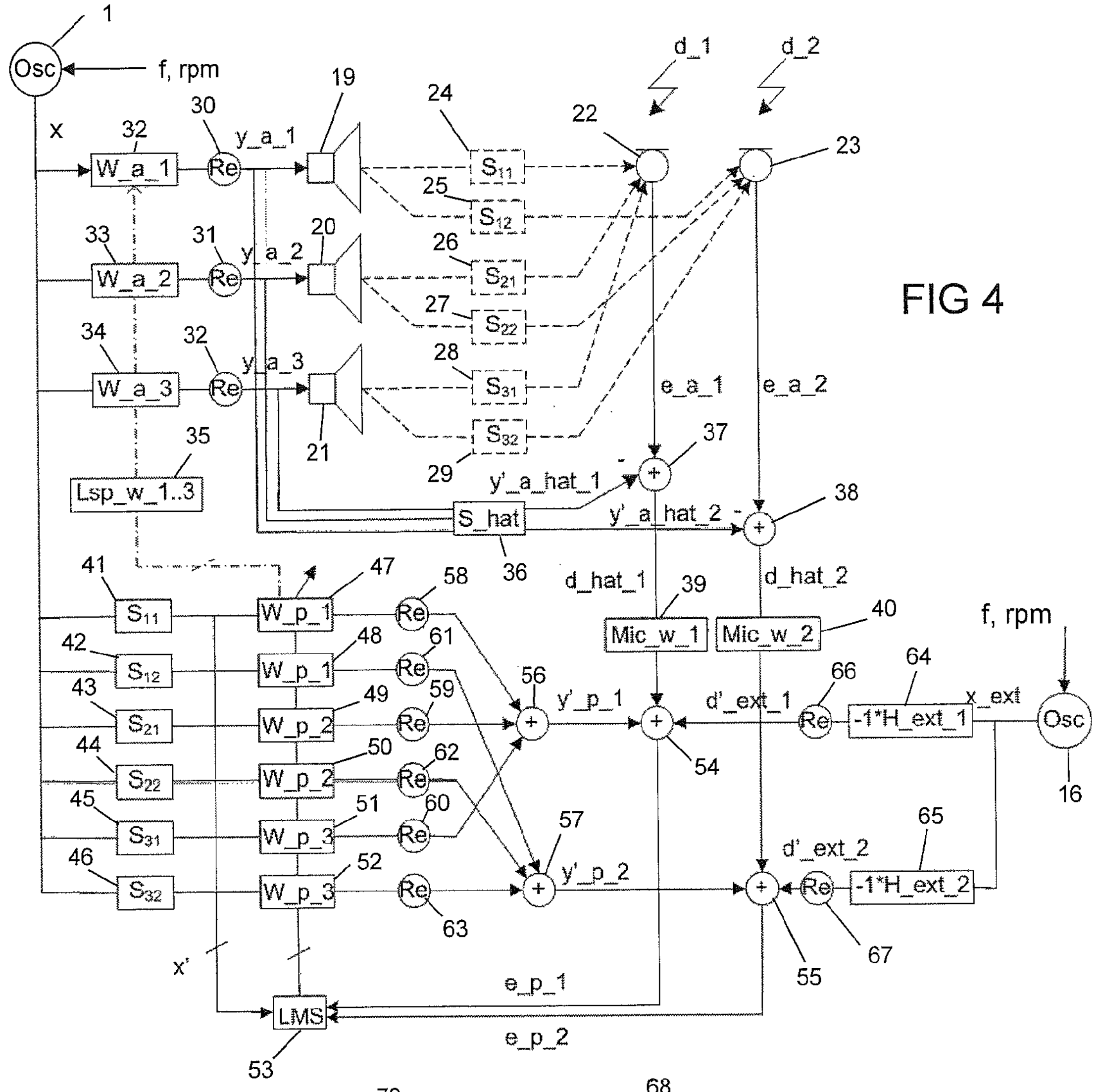
FIG. 4 is a block diagram illustration of a multi-channel feedforward ANC system.

As shown in FIG. 4, the system of FIG. 3 may be applied in a multi-channel ANC system that has, e.g., three loudspeakers 19, 20, 21 and two microphones 22, 23. The loudspeakers 19, 20, 21 and the microphones 22, 23 are arranged in different positions, thereby establishing six secondary paths 24-29 with transfer characteristics $S_{11}$, $S_{12}$, $S_{21}$, $S_{22}$, $S_{31}$, $S_{32}$ between each of the loudspeakers 19, 20, 21 and each of the microphones 22, 23. The microphones also receive disturbing noise d_1, d_2 at their respective positions. The loudspeakers 19, 20, 21 are each supplied with one of signals y_a_1, y_a_2, y_a_3, that are provided by real part processors 30, 31, 32 connected downstream of the filters 32, 33, 34. The filters 32, 33, 34 have transfer characteristics W_a_1, W_a_2, W_a_3 respectively, and are supplied with the reference noise signal x that is generated by the secondary noise source 1 as in the systems of FIGS. 1-3. The transfer characteristics W_a_1, W_a_2, W_a_3 are controlled by weighting elements 35. Furthermore, a filter block 36 having a transfer characteristic S_hat is connected downstream of the real part processors 30, 31, 32 and provides two output signals, i.e., signals y_a_hat_1, y_a_hat_2. The microphones 22, 23 provide error signals e_a_1, e_a_2 from which the signals y_a_hat_1, y_a_hat_2 are subtracted by the subtractors 37, 38, thereby providing signals d_hat_1, d_hat_2 that are supplied to the weighting elements 39, 40.

The reference noise signal x is also supplied to the filters 41-46 having transfer characteristics $S_{11}$, $S_{12}$, $S_{21}$, $S_{22}$, $S_{31}$, $S_{32}$ and subsequent controllable filters 47-52 having transfer characteristics W_p_1, W___1, W_p_2, W_p_2, W_p_3, W_p_3. The controllable filters 47-52 are controlled by a filter controller 53 that receives six signals x' from the filters 41-46 and two signals e_p_1, e_p_2 from adders 54, 55, respectively, to generate control signals for controlling the controllable filters 47-52. The adder 54 receives signal y'_p_1, signal d'_ext_1 and an output signal of the weighting element 39. The adder 55 receives signal y'_p_2, signal d'_ext_2 and an output signal of the weighting element 40. The signals y'_p_1, y'_p_2 are provided by adders 56, 57; the adder 56 receives via real part processors 58, 59, 60 the output signals of the filters 47, 49, 51 and the adder 57 receives via real part processors 61, 62, 63 the output signals of the filters 48, 50, 52. The signals d'_ext_1, d'_ext_2 are derived by filtering the signal x_ext from the external secondary noise source 16 with transfer characteristics −1·H_ext_1, −1·H_ext_2 of filters 64, 65 and taking the real parts thereof with real part processors 66, 67.

Figure 5:
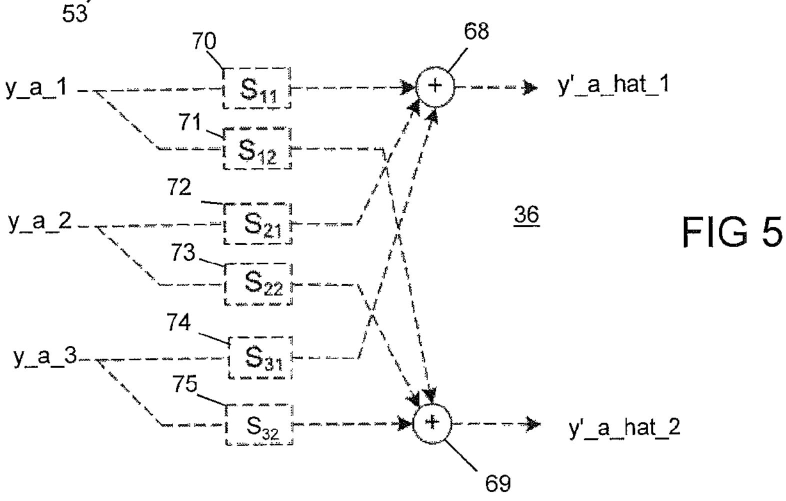
FIG. 5 is a block diagram illustration of a filter block used in the system of FIG. 4.

FIG. 5 depicts the filter block 36 in the system of FIG. 4 in more detail. The filter block 36 includes adders 68, 69 and filters 70-75 having the transfer characteristics $S_{11}$, $S_{12}$, $S_{21}$, $S_{22}$, $S_{31}$, $S_{32}$, respectively. Signal y_a_1 is supplied to the filters 70 and 71; signal y_a_2 is supplied to the filters 72 and 73; signal y_a_3 is supplied to the filters 74 and 75. The outputs of the filters 70, 72, 74 are supplied to the adder 68 and the outputs of the filters 71, 73, 75 are supplied to the adder 69. The adder 68 provides signal y'_a_hat_1 and the adder 69 provides signal y'_a_hat_2.

Figure 6:
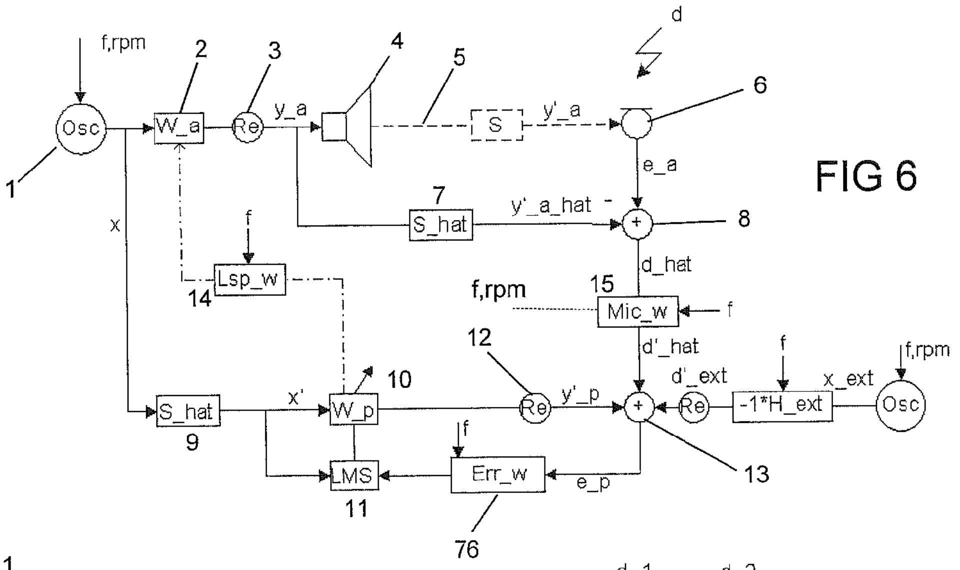
FIG. 6 is a block diagram illustration of a modified ANC system as shown in FIG. 3.

In FIG. 6, the ANC system of FIG. 3 is shown in which error signal input path of the filter controller 11 is modified. As can readily be seen, an error weighting element 76 having a weighting coefficient Err_w is connected between the adder 13 and the filter controller 11. The weighting coefficient Err_w is, as the weighting coefficients Lsp_w and Mic_of the weighting elements 14 and 15, dependent on parameters characterizing a particular noise situation, such as frequency $f_0$ or order frequency $f_m$, (and/or the revolutions per minute rpm).

Figure 7:
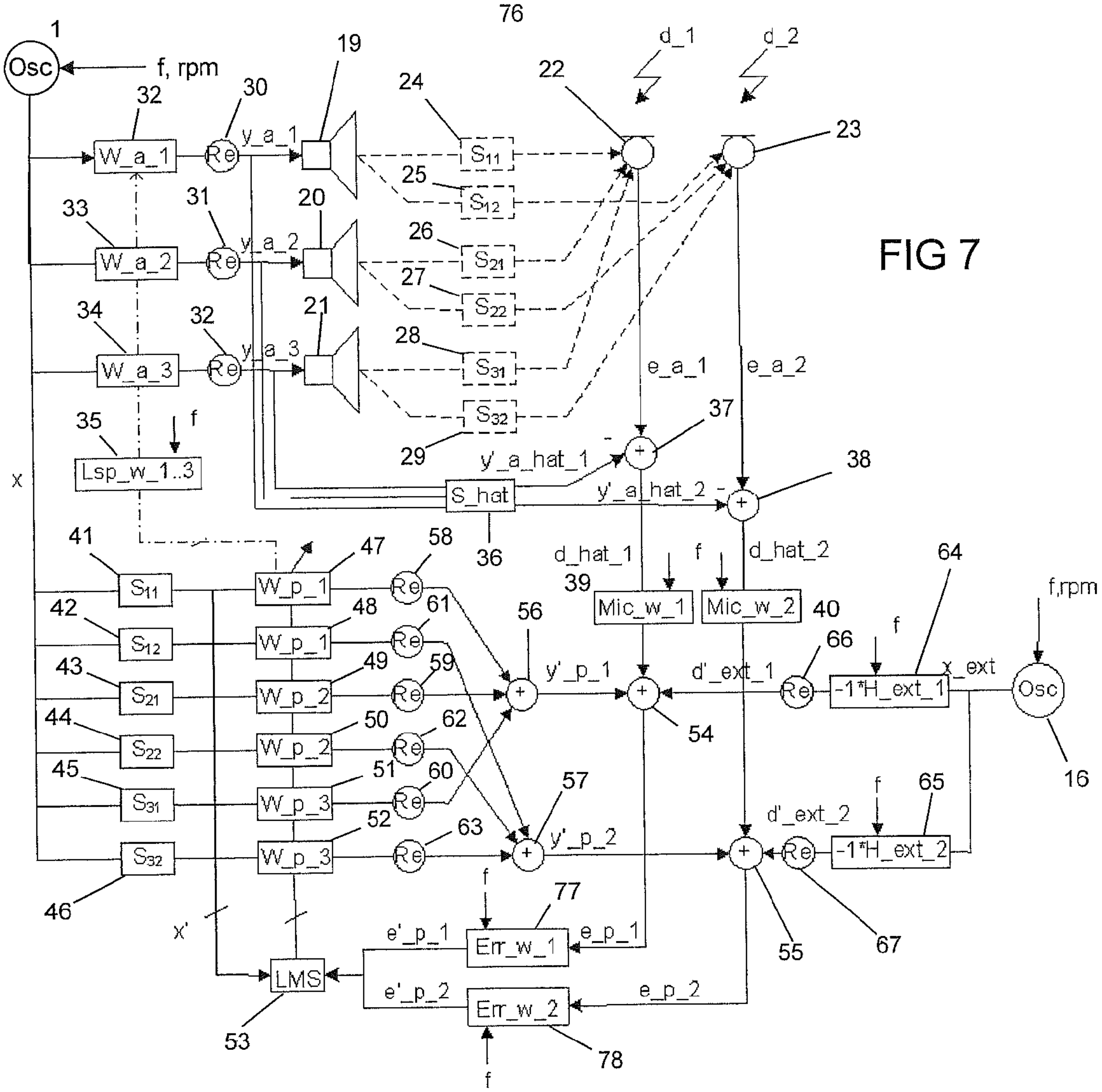
FIG. 7 is a block diagram illustration of a modified multi-channel feedforward ANC system as shown in FIG. 4.

A modified multi-channel feedforward ANC system based on the system of FIG. 4 is shown in FIG. 7. This system includes two error weighting elements 77 and 78, one 77 of which has a weighting coefficient Err_w_1 and is connected between the adder 54 and the filter controller 53, and the other 78 has a weighting coefficient Err_w_2 and is connected between the adder 55 and the filter controller 53. The weighting coefficients Err _w_1 and Err_w_2 are, as the weighting coefficients Lsp_w and Mic_w of the weighting elements 39 and 40, dependent on parameters characterizing a particular noise situation, such as frequency f (and/or the revolutions per minute rpm). The error weighting elements 77 and 78 provide weighted error signals e'_p_1 and e'_p_2 to the filter controller 53.

Deactivation of noise reduction to "0 dB" in the way described above using weighting coefficients does not mean that ANC is deactivated at the microphone or listening positions. There is still some control present because the system is forced to "0 dB". When, for instance, an attenuation of "0 db" is desired at a particular microphone position, the ANC system in connection with all its loudspeakers seeks to maintain the instant noise signal d as it is, to the effect that the signals output by the loudspeakers are considered as noise by the ANC system at this point and a compromise has to be made in the ANC system's adaption procedure. Attenuation is desired for each of the remaining microphone signals, however, these signals exhibit a negative effect on the signal of the "0 dB" microphone. For the ANC system, this is a contradiction in itself and the state reached by the ANC system relies heavily on the loudspeaker microphone paths. In particular situations, it may be desirable to deactivate in terms of ANC one of the microphones 22, 23 in FIG. 7 or the microphone 6 in FIG. 6. Deactivation means here that the ANC system does not want to "know" what happens on the microphone or listening position and it does not take into regard what is happening there with the noise d. The ANC system provides no control at that particular position.

A method of achieving this is to weight (multiply) the error signals e_p_1 and e_p_2 with the weighting coefficients Err_w_1 and Err_w_2 as can be seen in FIG. 7. The weighted error signals e'_p_1 and e'_p_2 resulting therefrom are supplied to the LMS controller 53 for adaption of the filters 32, 33, 34 and 47-52. For instance, a weighting coefficient of "0" causes deactivation of the microphone (and the corresponding listening position) and a weighting coefficient of "1" causes its full activation. Accordingly, the transfer characteristics of adaptive filters for the loudspeakers/channels of the described multi-channel system employing LMS algorithm can be described as follows:

$$W\_p\_1[n+1]=W\_p\_1[n]+\mu\cdot(x'_{11}\cdot e'\_p\_1+x'_{12}\cdot e'\_p\_2)$$

$$W\_p\_2[n+1]=W\_p\_2[n]+\mu\cdot(x'_{21}\cdot e'\_p\_1+x'_{22}\cdot e'\_p\_2)$$

$$W\_p\_3[n+1]=W\_p\_3[n]+\mu\cdot(x'_{31}\cdot e'\_p\_1+x'_{32}\cdot e'\_p\_2)$$

$$e'\_p\_1=Err\_w\_1\cdot e\_p\_1$$

$$e'\_p\_2=Err\_w\_2\cdot e\_p\_2.$$

Figure 8:
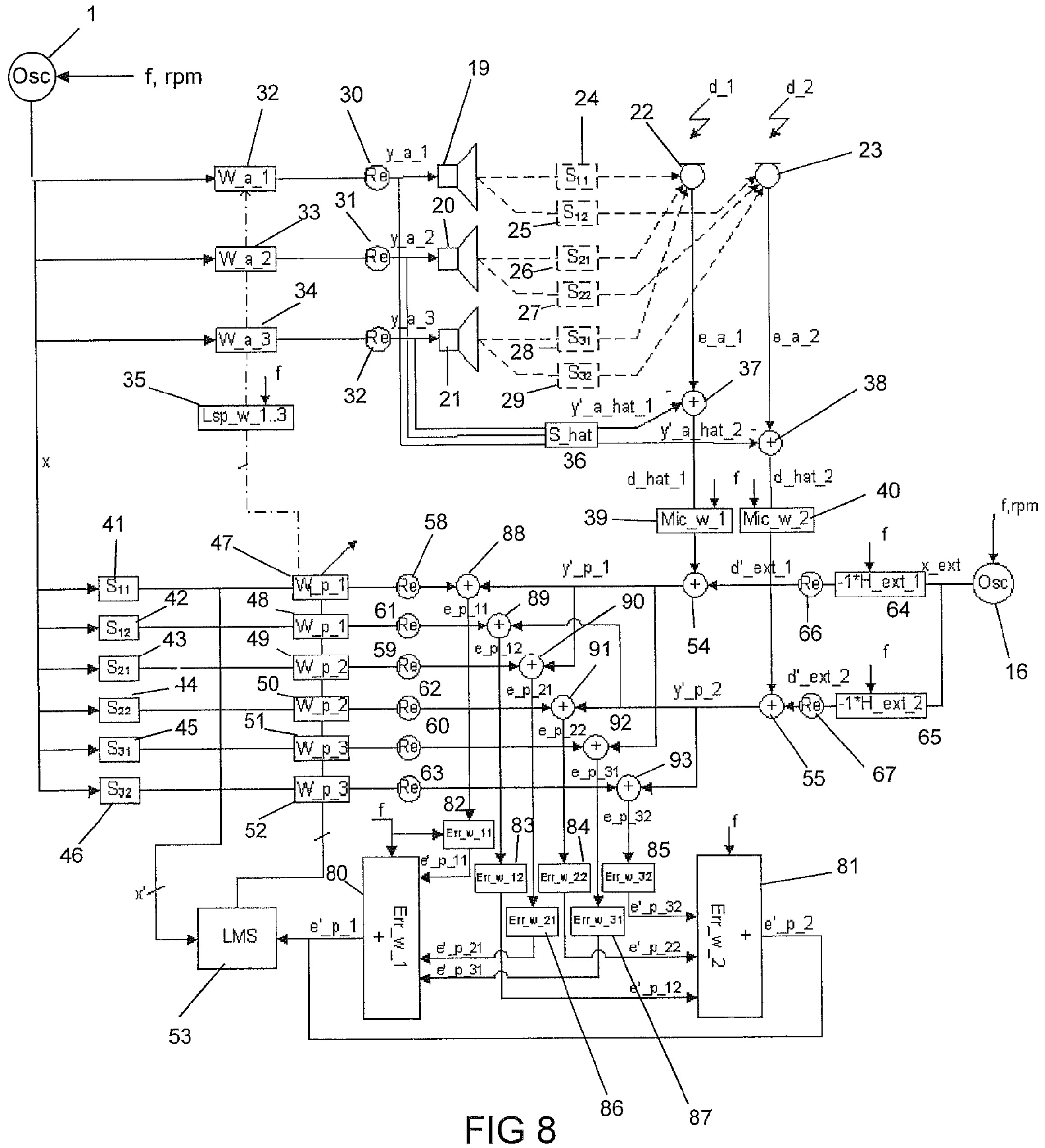
FIG. 8 is a block diagram illustration of a modified multi-channel feedforward ANC system as shown in FIG. 7.

With adequate determination of the weighting coefficients activation or deactivation of a particular microphone can be established to the effect that only a certain share of the respective microphone signal contributes to adaption. According to the above equations, all loudspeakers are affected by equal microphone weighting coefficients during adaption. For even more control options and flexibility, the system may be enhanced by additional weighting of the loudspeaker signals as shown in FIG. 8. In the present example, this leads to six additional weighting coefficients (i.e., two for the microphone multiplied with three for the loudspeakers); the coefficients are Err_w_1, Err_w_2, Err_w_11, Err_w_12, Err_w_21, Err_w_22, Err_w_31, Err_w_32 and may be stored as look-up table for different frequencies f. For the system of FIG. 8 the following equations apply:

$$W\_p\_1[n+1]=W\_p\_1[n]+\mu\cdot(x'_{11}\cdot e'\_p\_1+x'_{12}\cdot e'\_p\_2)$$

$$W\_p\_2[n+1]=W\_p\_2[n]+\mu\cdot(x'_{21}\cdot e'\_p\_1+x'_{22}\cdot e'\_p\_2)$$

$$W\_p\_3[n+1]=W\_p\_3[n]+\mu\cdot(x'_{31}\cdot e'\_p\_1+X'_{32}\cdot e'\_p\_2)$$

$$e'\_p\_1=Err\_w\_1\cdot(e\_p\_11+e'\_p\_p\_21+e'\_p\_31)$$

$$e'\_p\_2=Err\_w\_2\cdot(e\_p\_21+e'\_p\_p\_22+e'\_p\_32)$$

$$e'\_p\_11=Err\_w\_11\cdot e\_p\_11 \text{ and so on.}$$

FIG. 8 shows a modified multi-channel feedforward ANC system based on the system of FIG. 7, in which, in contrast to the system of FIG. 7, the two error signals e'_p_1 and e'_p_2 are provided by two weighting elements 80 and 81 that receive error signals e'_p_11, e'_p_21, e'_p_31, and e'_p_12, e'_p_22, e'_p_32, respectively, and multiply the sum of those signals as set forth in the above equations. Accordingly, the signals e'_p_11, e'_p_21, e'_p_31, and e'_p_12, e'_p_22, e'_p_32 are derived from signals e_p_11, e_p_21, e_p_31, and e_p_12, e_p_22, e_p_32 by multiplication with weighting coefficients Err_w_11, Err_w_21, Err_w_31, and Err_w_12 Err_w_22, Err_w_32. The multiplications are performed by weighting elements 82-87, in which coefficient Err_w_11 is assigned to element 82, Err_w_12 is assigned to element 83, Err_w_22 is assigned to element 84, Err_w_32 is assigned to element 85, Err_w_11 is assigned to element 86, and Err_w_31 is assigned to element 87. Signals e_p_11, e_p_21, e_p_31, and e_p_12, e_p_22, e_p_32 are provided by adders 88, 90 92 and 89, 91, 93 that add signals output by the real processors 58, 59, 60 to the signal y'_p_l from the adder 54 and that add signals output by the real processors 61, 62, 63 to the signal y'_p_2 from the adder 55. All coefficient elements 80-87 are controlled by the frequency f. Adequate determination of the weighting coefficients allows for a concentration of the ANC system's effects to certain positions, e.g., within a vehicle cabin, so that, for instance, better noise control is present at the driver's position at certain revolutions per minute. In the system of FIG. 8, all weighting elements are controlled by the frequency f. However, all or some of the weighting elements may optionally be not controllable, or additionally or alternatively controlled by the revolutions per minute rpm, or controlled by any other parameter characterizing the noise source. In case the weighting coefficients are constant, i.e., not controllable by parameters characterizing the noise source(s), the coefficients may be selectable by a listener/user.

The systems disclosed herein, in particular their signal processing units such as filters, adders, subtractors, weighting elements etc., may be realized in dedicated hardware and/or in programmable (digital) hardware such as microprocessors, signal processors, microcontrollers or the like, under adequate software-based control. Such a program, i.e., its instructions, may be stored in an adequate memory (or any other computer-readable medium) and are read out for controlling the microprocessor hardware or at least parts thereof to perform the function (method) of certain processing units (e.g., filter, adder, subtractor, weighting element) per se and in combination with other units.

Although various examples of realizing the invention have been disclosed, it will be apparent to those skilled in the art that various changes and modifications can be made which will achieve some of the advantages of the invention without departing from the spirit and scope of the invention. It will be obvious to those reasonably skilled in the art that other components performing the same functions may be suitably substituted. Such modifications to the inventive concept are intended to be covered by the appended claims.

Although the present invention has been illustrated and described with respect to several preferred embodiments thereof, various changes, omissions and additions to the form and detail thereof, may be made therein, without departing from the spirit and scope of the invention.

What is claimed is:

1. An active noise control system for tuning an acoustic noise signal at a listening position, the system comprises:

a microphone that converts acoustic signals into electric signals and that is arranged at the listening position;

a loudspeaker that converts electrical signals into acoustic signals and that radiates a noise cancelling signal via a secondary path to the microphone;

a noise source that generates an electrical noise signal modeling the acoustic noise signal;

a first filter that has a controllable first transfer characteristic and that is connected between the noise source and the loudspeaker;

a second filter that has a second transfer characteristic and that is connected downstream of the noise source;

a third filter that has a controllable third transfer characteristic and that is connected downstream of the second filter;

a noise signal estimator that is connected downstream of the microphone and that provides an estimate of the acoustic noise signal; and an adaptive filter controller that is downstream of the second filter and downstream of the noise signal estimator and that controls the transfer characteristic of the third filter; in which the second transfer characteristic is an estimation of the transfer characteristic of the secondary path;

the first transfer characteristic is controlled by the third transfer characteristic via a filter coefficient copy path; and a first weighting element is connected into the filter coefficient copy path and/or a second weighting element is connected downstream of the noise signal estimator.

2. The system of claim 1, in which the noise signal estimator comprises a fourth filter that has a fourth transfer characteristic and that is connected downstream of the first filter, and a subtractor that is connected downstream of the microphone and the fourth filter and that provides the estimated noise signal; the fourth transfer characteristic being an estimate of the transfer characteristic of the secondary path.

3. The system of claim 1, further comprising an additional noise source that is connected upstream of the adaptive filter controller.

4. The system of claim 3, in which a fifth filter is connected downstream of the additional noise source.

5. The system of claim 4, in which at least one of the first, third, and fifth filters is a complex filter and in which a real part processor is connected downstream of such complex filter.

6. The system of claim 4, in which an adder is connected downstream of the third filter, downstream of the third weighting element and upstream of the adaptive filter controller.

7. The system of claim 4, in which the first and second weighting elements comprise multipliers that multiply the filter coefficients to be copied or the signal from the subtractor, respectively, with weighting coefficients.

8. The system of claim 7, in which the weighting coefficients are constant and are selectable by a listener.

9. The system of claim 7, in which the weighting coefficients for at least one weighting element are stored in a look-up table.

10. The system of claim 9, in which different weighting coefficients for different noise situations are stored and the coefficients are read out depending on the instantaneous vehicle condition.

11. The system of claim 10, wherein the noise source is a motor of a vehicle and the parameters include at least one of revolutions per minute and/or the fundamental frequency of the motor.

12. The system of claim 1, in which the noise source is controlled by parameters of a source generating the acoustic noise signal.

13. The system of claim 1, in which the adaptive filter controller comprises an error signal input and in which a third weighting element is connected upstream of the error signal input.

14. An active noise control method for tuning an acoustic noise signal at a listening position, the method comprises:

converting acoustic signals at the listening position into electric signals;

generating an electrical noise signal modeling the acoustic noise signal;

filtering the electrical noise signal that models the acoustic noise signal with a controllable first transfer characteristic, thereby providing a first filtered noise signal;

converting the first filtered noise signal into an audio signal which is radiated via a secondary path to the listening position;

filtering the electrical noise signal that models the acoustic noise signal with a second transfer characteristic, thereby providing a second filtered noise signal;

adaptively filtering with a third transfer characteristic the second filtered noise signal;

providing an estimate of the acoustic noise signal from the converted acoustic signal at the listening position in which the second transfer characteristic is an estimate of the transfer characteristic of the secondary path;

the first transfer characteristic is controlled by the third transfer characteristic via a filter coefficient copy path; and a first weighting process is performed in the filter coefficient copy path and/or a second weighting process is applied to the estimate of the acoustic noise signal.

15. A tunable active noise control system, comprising:

a source that provides a noise signal;

a first adaptive filter that receives and filters the noise signal to provide a filtered noise signal;

a loudspeaker that receives the filtered noise signal and provides an audio signal indicative thereof to a listening location;

a microphone that senses audio at the listening location and provides a sensed audio signal indicative thereof;

a first filter that receives and processes the filtered noise signal to provide a first filtered signal;

a first summer that receives the sensed audio signal and the first filtered signal and provides a first difference signal indicative of the difference thereof;

a second filter that receives the noise signal and provides a second filtered signal;

a second adaptive filter that receives and filters the second filtered signal to provide a second adaptive filter output signal, wherein the second adaptive filter comprises tap weights that are set as a function of the second filtered signal and an error signal;

a first weighting unit that provides a weighting value to the output of the first and second adaptive filters;

a second weighting unit that applies a second weighting value to the first difference signal to provide a weighted first difference signal; and a second summer that receives the weighted first difference signal and a signal indicative of the second adaptive filter output signal, and provides the error signal indicative of the difference between the weighted first difference signal and the signal indicative of the second adaptive filter output signal.

* * * * *